(12) United States Patent
Kim et al.

(10) Patent No.: US 8,840,895 B2
(45) Date of Patent: Sep. 23, 2014

(54) HUMAN ANTIBODIES SPECIFICALLY BINDING TO THE HEPATITIS B VIRUS SURFACE ANTIGEN

(75) Inventors: Se-Ho Kim, Yongin-si (KR); Ki Hwan Chang, Yongin-si (KR); Kwang-Won Hong, Yongin-si (KR); Yong-Won Shin, Yongin-si (KR); Min-soo Kim, Yongin-si (KR); Hae-Won Lee, Yongin-si (KR); Kyung Hwan Ryoo, Yongin-si (KR); Dong Hyuck Seo, Yongin-si (KR); Jean Man Kim, Yongin-si (KR); Yong Nam Shin, Yongin-si (KR); Sunmi Koo, Yongin-si (KR); Jung-Ae Lim, Yongin-si (KR); Mijung Lee, Yongin-si (KR); Yeon Kyung Lee, Yongin-si (KR); Misun Seo, Yongin-si (KR)

(73) Assignee: Green Cross Corporation, Gyeonggi-Do (KR)

( * ) Notice: Subject to any disclaimer, the term of this patent is extended or adjusted under 35 U.S.C. 154(b) by 0 days.

(21) Appl. No.: 13/518,683

(22) PCT Filed: Jul. 8, 2010

(86) PCT No.: PCT/KR2010/004445
§ 371 (c)(1),
(2), (4) Date: Jun. 22, 2012

(87) PCT Pub. No.: WO2011/078456
PCT Pub. Date: Jun. 30, 2011

(65) Prior Publication Data
US 2012/0264921 A1    Oct. 18, 2012

(30) Foreign Application Priority Data

Dec. 24, 2009  (KR) .................. 10-2009-0130900

(51) Int. Cl.
| *A61K 39/42* | (2006.01) |
| *C12N 5/07* | (2010.01) |
| *C07H 21/04* | (2006.01) |
| *C07K 16/08* | (2006.01) |
| *A61K 39/00* | (2006.01) |

(52) U.S. Cl.
CPC ........... *C07K 16/082* (2013.01); *C07K 2317/21* (2013.01); *A61K 2039/505* (2013.01)
USPC ....................... 424/159.1; 435/328; 536/23.53

(58) Field of Classification Search
CPC ............. A61K 39/42; A61K 2039/505; C07K 2317/21
USPC ......................................................... 530/389
See application file for complete search history.

(56) References Cited

FOREIGN PATENT DOCUMENTS

| KR | 10-2004-0084875 A | 10/2004 |
| KR | 10-0467706 B1 | 1/2005 |
| KR | 10-2009-0056537 A | 6/2009 |
| WO | 2009/069917 A1 | 6/2009 |

OTHER PUBLICATIONS

Shin et al., Human monoclonal antibody against Hepatitis B virus surface antigen (HBsAg), Antiviral Research, 2007, 75:113-120.*
Shin et al., "Human Monoclonal Antibody Against Hepatitis B Surface Antigen (HBsAg)," Antiviral Research, 2007, vol. 75, pp. 113-120.
Kim et al., "Neutralization of Hepatitis B Virus (HBV) by Human Monoclonal Antibody Against HBV Surface Antigen (HBsAg) in Chimpanzees," Antiviral Research, 2008, p. 188-191.
Zhang et al., "Neutralization Epitope Responsible for the Hepatitis B Virus Subtype-Specific Protection in Chimpanzees," PNAS, 2006, vol. 103, No. 24, pp. 9214-9219.
Kim et al., "Selection and Characterization of Human Antibodies Again Hepatitis B Virus Surface Antigen (HBsAg) by Phage-Display," 2002, Hybridoma and Hybridomics, vol. 21, No. 5, pp. 385-392.
Japanese Patent Office, Japanese Office Action issued in corresponding JP Application No. 2012-545832, dated Nov. 5, 2013.
Directorate General of Intellectual Property Rights of Indonesia, Communication dated Feb. 4, 2014 issued in the corresponding Indonesian Patent Application No. W00201202887.

* cited by examiner

*Primary Examiner* — Zachariah Lucas
*Assistant Examiner* — Barry A Chestnut
(74) *Attorney, Agent, or Firm* — Sughrue Mion, PLLC

(57) ABSTRACT

Provided are antibodies specifically binding to the HBV surface antigen (HBsAg) which are effective for the prevention or treatment of hepatitis B.

2 Claims, 12 Drawing Sheets

FIG. 4

```
                    1                                                                           84
HB48-33      (1)    QVQLVQSGGEVKKPGALMKVSCKASGYIFTSYGISWVRQAPGQGLEWIGWINTYSGHTNYARKFQRVTMTWDTSTSTAYMELS
HB48-35      (1)    QVQLVQSGGEVKKPGALMKVSCKASGYIFTSYGISWVRQAPGQGLEWIGWINTYSGHTNYARKFQRVTMTWDTSTSTAYMELS
HB48-59      (1)    QVQLVQSGGEVKKPGALMKVSCKASGYIFTSYGISWVRQAPGQGLEWIGWINTYSGHTNYARKFQRVTMTWDTSTSTAYMELS
Consensus    (1)    QVQLVQSGGEVKKPGALMKVSCKASGYIFTSYGISWVRQAPGQGLEWIGWINTYSGHTNYARKFQRVTMTWDTSTSTAYMELS 85                                                                          168
HB48-33     (85)    SLRSDDTAVYYCARVPTWGIDYWGQGTLVTVSSGGGGSGGGGSGGGGSQAGLYQ-PPSVSVAPGKTARITCGIN-----IGRK
HB48-35     (85)    SLRSDDTAVYYCARVPTWGIDYWGQGTLVTVSSGGGGSGGGGSGGGGSEIVLTQSPPSLSASVGDRVTITCASQ-----DINN
HB48-59     (85)    SLRSDDTAVYYCARVPTWGIDYWGQGTLVTVSSGGGGSGGGGSGGGGSDIVMTQTPLSLPVTPGEPASISCRSSQSLLHSNGYN
Consensus   (85)    SLRSDDTAVYYCARVPTWGIDYWGQGTLVTVSSGGGGSGGGGSGGGGS         PPSVSVSPGD  ASITC  ASQ     G  N 169                                                                         246
HB48-33    (163)    SVHWYQQKTGQAPVLVVEDNKRPSGIPERFSGSNSGNTATLTISGTQAMDEALYYCQAWDSST-VVFGGGTKLTVLG
HB48-35    (164)    NVNWFQQEPGKAPRLLIYDASNLCTGVPSRFSGSGSGTEFTLTISSLQPEDFATYYCQQTSVP-LTFGGGTKVDIKR
HB48-59    (169)    YLDWYLQKPGQSPQILIYLGSKRASGVPDRFSGSGSGTDFTLQISRVEAEDVGVYYCMQSTQFPPYTFGQSTKLEIKR
Consensus  (169)    V WYQQKPGQAP LLIYDASKR SGVPDRF SGSGSGTDFTLTIS LQAED A YYCQQSS FP LTFGGSTKLDIKR
```

FIG. 11
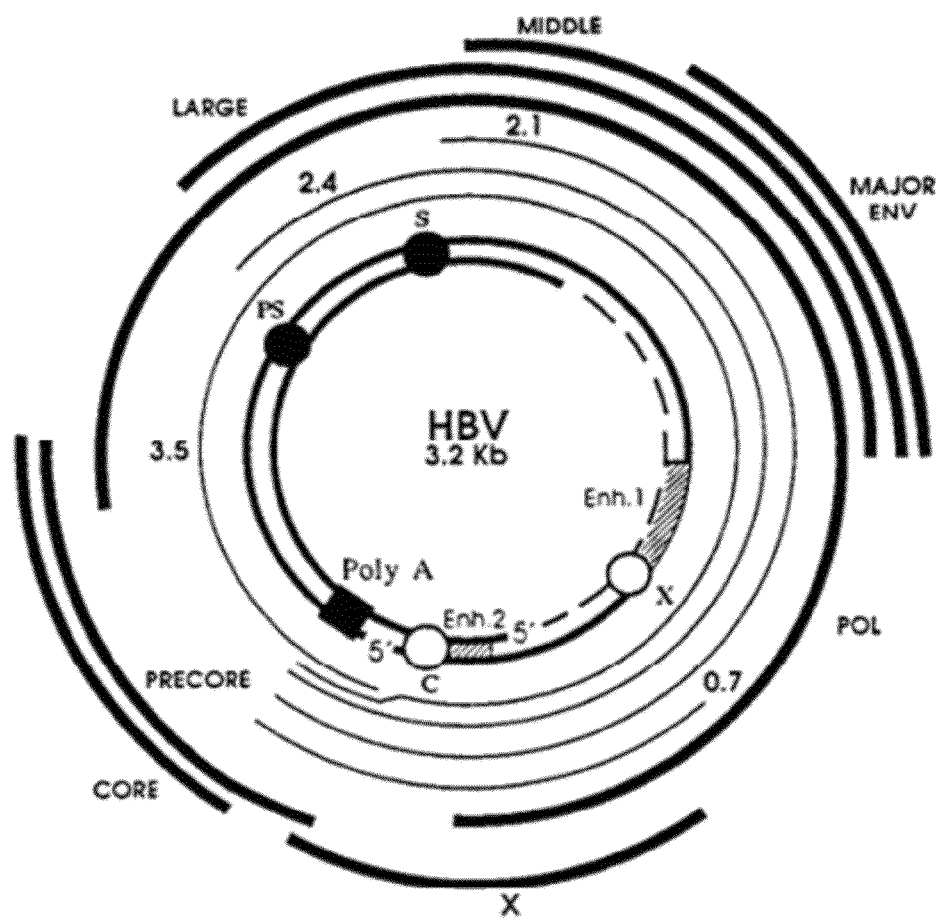
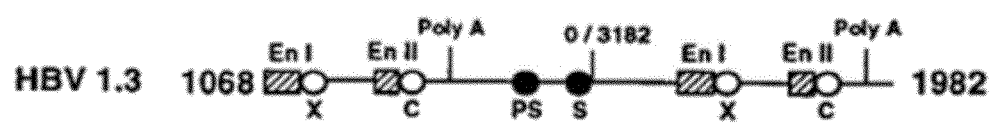

HUMAN ANTIBODIES SPECIFICALLY BINDING TO THE HEPATITIS B VIRUS SURFACE ANTIGEN

CROSS REFERENCE TO RELATED APPLICATION

This application is a National Stage of International Application No. PCT/KR2010/004445, filed Jul. 8, 2010, claiming priority based on Korean Patent Application No. 10-2009-0130900 filed Dec. 24, 2009, the contents of all of which are incorporated herein by reference in their entirety.

FIELD OF THE INVENTION

The present invention relates to antibodies specifically binding to the hepatitis B virus surface antigen (HBsAg).

BACKGROUND OF THE INVENTION

Hepatitis B virus (HBV) is a member of the Hepadnavirus family, and causes acute and chronic hepatitis. About 350 million people of the world's population, in particular, 5~8% of the people in Korea and China, are chronic HBV patients, and HBV is a main cause of liver diseases and liver cancer. Although the development of a vaccine against HBV has made it possible to prevent hepatitis B, but still many people are suffering from chronic hepatitis by HBV infection. The HBV infection induces hepatitis and liver cirrhosis as well as liver cancer, and the incidence of liver cancer in chronic hepatitis patients is 300 fold higher than the normal. The WHO (World Health Organization) revealed that about 80% of liver cancers result from chronic hepatitis B by HBV infection.

Currently available therapeutic drugs for hepatitis B include nucleoside analogues, such as lamivudine, adefovir dipivoxil, and others, and they are known to inhibit HBV DNA polymerase. However, resistant viruses emerge in 75% of the patients after three-years of administration therewith, leading to decreased therapeutic efficacies, and thus, they are used in combination with hepatitis B antibody agents so as to prevent vertical transmission or infection after liver transplantation.

The hepatitis B antibody agents currently used are prepared from human blood sources having anti-HBV antibodies using highly technical purification and virus inactivation methods, but such methods cannot meet the ever-rising demand due to the low availability of expensive human plasma with high anti-HBV antibody as well as the high cost of inactivating the plausible human plasma-derived viruses.

Ever since a methodology of preparing a monoclonal antibody (mAb) was established by Köhler and Milstein (1975), monoclonal antibodies derived from mice have been mainly used for diagnosis or some treatment. However, the mouse antibody cannot be administered due to possible generation of human anti-mouse antibody (HAMA) when applied to a human body for therapeutic purpose. In order to solve the problems of HAMA, there have been developed chimeric and humanized antibodies. The chimeric antibody contains the variable regions (Fv fragment) of mouse mAb which constitutes ~30% of whole antibody molecule. In contrast, the humanized antibody contains the CDRs (complementarity determining regions) of mouse mAb which constitutes ~10% of whole antibody molecule. Although such chimeric and humanized antibodies reduced the HAMA reaction significantly, it might be better to use human antibodies in the treatment of chronic disease such as chronic hepatitis which requires a long-term and continuous administration.

The present invention has endeavored to develop novel, improved antibodies and found that such antibodies can be used to inactivate HBV by binding to the HBV-surface antigen.

SUMMARY OF THE INVENTION

Therefore, it is an object of the present invention to provide a novel antibody which specifically binds to hepatitis B virus surface antigen.

It is another object of the present invention to provide DNAs which respectively encode the heavy chain variable region and the light chain variable region of said antibody, and an expression vector comprising the same.

It is still another object of the present invention to provide a cell line transformed with the expression vector.

It is a further object of the present invention to provide a pharmaceutical composition for preventing or treating hepatitis B, comprising said antibody.

In accordance with one aspect of the present invention, there is provided an antibody specifically binding to hepatitis B virus surface antigen (HBsAg), comprising: a) a heavy chain variable region having the amino acid sequence of SEQ ID NO: 1; b) a light chain variable region having any of the amino acid sequences of SEQ ID NOs: 2, 3, and 4; c) a heavy chain constant region; and d) a light chain constant region.

In accordance with another aspect of the present invention, there is provided a DNA which encodes the heavy chain variable region having the amino acid sequence of SEQ ID NO: 1 or the light chain variable region having any of the amino acid sequences of SEQ ID NOs: 2, 3, and 4, and an expression vector comprising the same.

In accordance with a still another aspect of the present invention, there is provided a cell line transformed with said expression vector.

In accordance with a further aspect of the present invention, there is provided a composition for preventing or treating hepatitis B, comprising said antibody.

BRIEF DESCRIPTION OF THE DRAWINGS

The above and other objects and features of the present invention will become apparent from the following description of the invention, when taken in conjunction with the accompanying drawings, which respectively show:

FIG. 4: amino acid sequences of the single chain variable fragments (scFv) of the inventive antibodies selected from an antibody library;

FIG. 11: a map of vector pHBV1.3-MBRI prepared from pcDNA3.1 by inserting a HBV DNA sequence, the vector being used in the preparation of a mouse model of acute hepatitis B;

DETAILED DESCRIPTION OF THE INVENTION

Hereinafter, the present invention is described in detail.

The present invention provides an antibody specifically binding to hepatitis B virus surface antigen (HBsAg), comprising: a) a heavy chain variable region having the amino acid sequence of SEQ ID NO: 1; b) a light chain variable region having any of the amino acid sequences of SEQ ID NOs: 2, 3, and 4; c) a heavy chain constant region; and d) a light chain constant region. The antibody of the present invention is characterized by the efficacy in preventing or treating hepatitis B by specifically binding to hepatitis B virus surface antigen to inactivate HBV.

The antibodies specifically binding to the HBV surface antigen may be preferably selected by modification of a phage display method (Smith, Science, 228, 1315-1317, 1985; and Hoogenboom & Chames, Immunol Today, 21, 371-378, 2000). In the phage display method, a gene (gene III) encoding a surface protein of filamentous phage (e.g. M13, Fd or Fl) is fused with a gene encoding an antibody of interest, to produce virus particles having a fused antibody exposed on the surface which is of an antibody-phage form. Subsequently, an antibody of interest can be selected from a phage library through the biopanning technique using high specificity and affinity of the antibody and high infective property of the phage (Burton & Barbas, Adv. Immunol., 57, 191-280, 1994; Winter et al., Annu. Rev. Immunol., 12, 433-455, 1994; and Hoogenboom et al., Immunotechnology, 4, 1-20, 1998; Kim et al., Hybrid Hybridomics, 21, 385-392, 2002). The phage display vector may be pKS4H (see Korean Patent No. 0635370) or pCANTAB5E, preferably, pKS4H.

Figure 10:
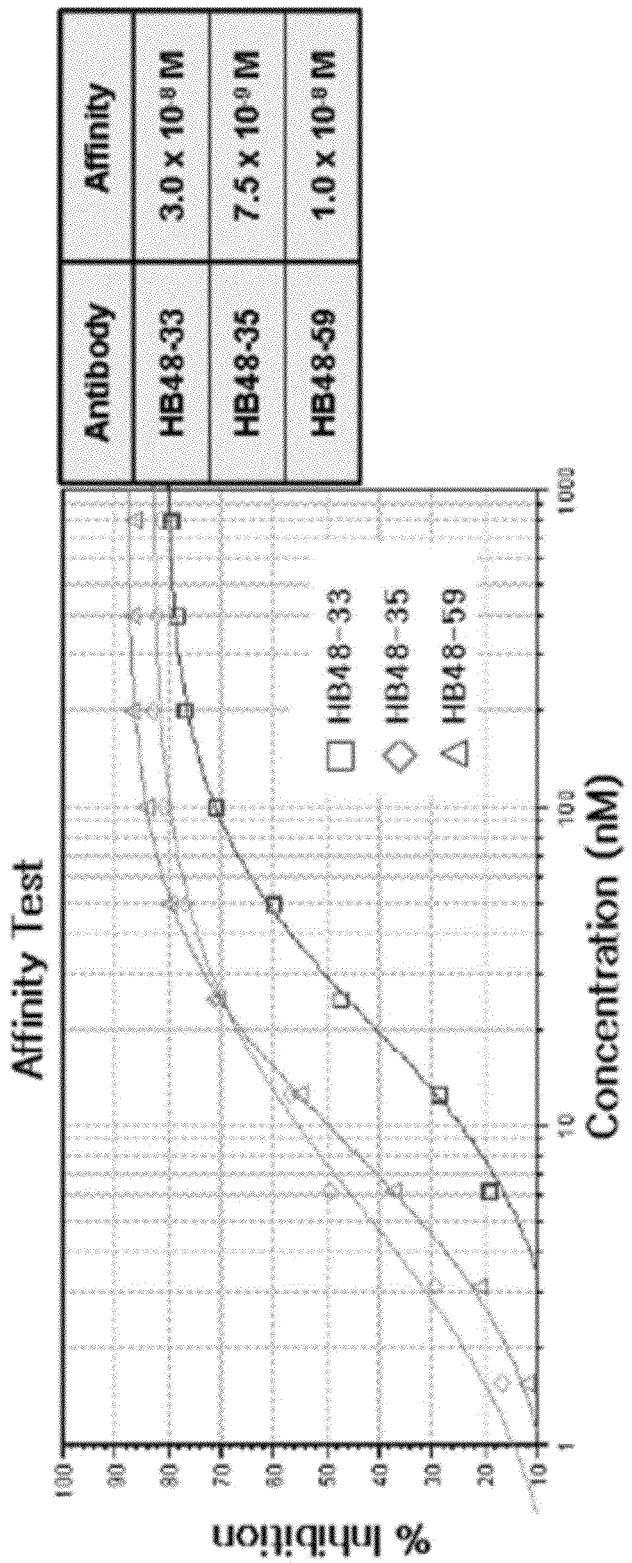
FIG. 10: relative affinities of the human antibodies (HB48-33, HB48-35, and HB48-59) to the HBV surface antigen.

The present inventors have selected three human antibodies (HB48-33, HB48-35, and HB48-59) from a phage library, and then examined the affinity of antibodies and neutralizing ability against the HBV surface antigen (FIGS. 10 and 11). Additionally, amino acid sequences of the variable regions of heavy and light chains were analyzed, and then it was confirmed that all heavy chain variable regions have the amino acid sequence of SEQ ID NO: 1 and light chain variable regions have the amino acid sequences of SEQ ID NO: 2, 3, and 4, respectively.

The constant regions of heavy chain and light chains of the inventive antibodies may be identical to those of a human antibody.

The present invention provides a DNA encoding the antibody heavy chain variable region having the amino acid sequence of SEQ ID NO: 1. Preferably, the DNA may comprise the polynucleotide having the nucleotide sequence of SEQ ID NO: 5 encoding the amino acid sequence of SEQ ID NO: 1.

The present invention provides a DNA encoding the antibody light chain variable region having any of the amino acid sequences of SEQ ID NOs: 2, 3, and 4. Preferably, the DNA may comprise the polynucleotide having any of the nucleotide sequences of SEQ ID NOs: 6, 7, and 8 encoding the amino acid sequences of SEQ ID NOs: 2, 3, and 4.

Figure 5:
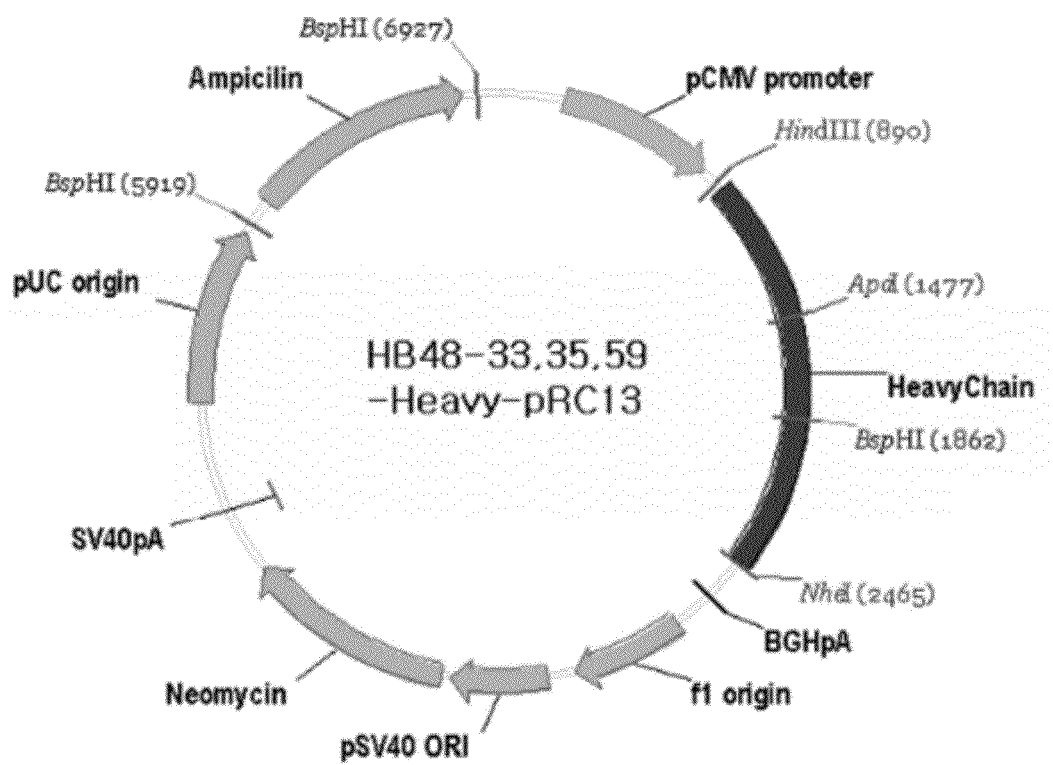
FIG. 5: a map of the expression vector for expressing the heavy chain of the human antibody of the present invention, HB48-33-Heavy-pRC13, HB48-35-Heavy-pRC13, or HB48-59-Heavy-pRC13.

The present invention provides an expression vector for expressing the heavy chain variable region of the antibody specifically binding to the HBV surface antigen, comprising the DNA encoding the heavy chain variable region of the antibody. Preferably, the expression vector may be "HB48-33-Heavy-pRC13", "HB48-35-Heavy-pRC13", or "HB48-59-Heavy-pRC13" whose map is depicted in FIG. 5.

Specifically, the vector may be prepared by inserting the VH fragment (HB48VH) of the antibody selected by panning process into a suitable vector, e.g., pRC13 vector (deposit No. KCLRF-BP-00054; Korean Patent No. 523732).

Figure 6:
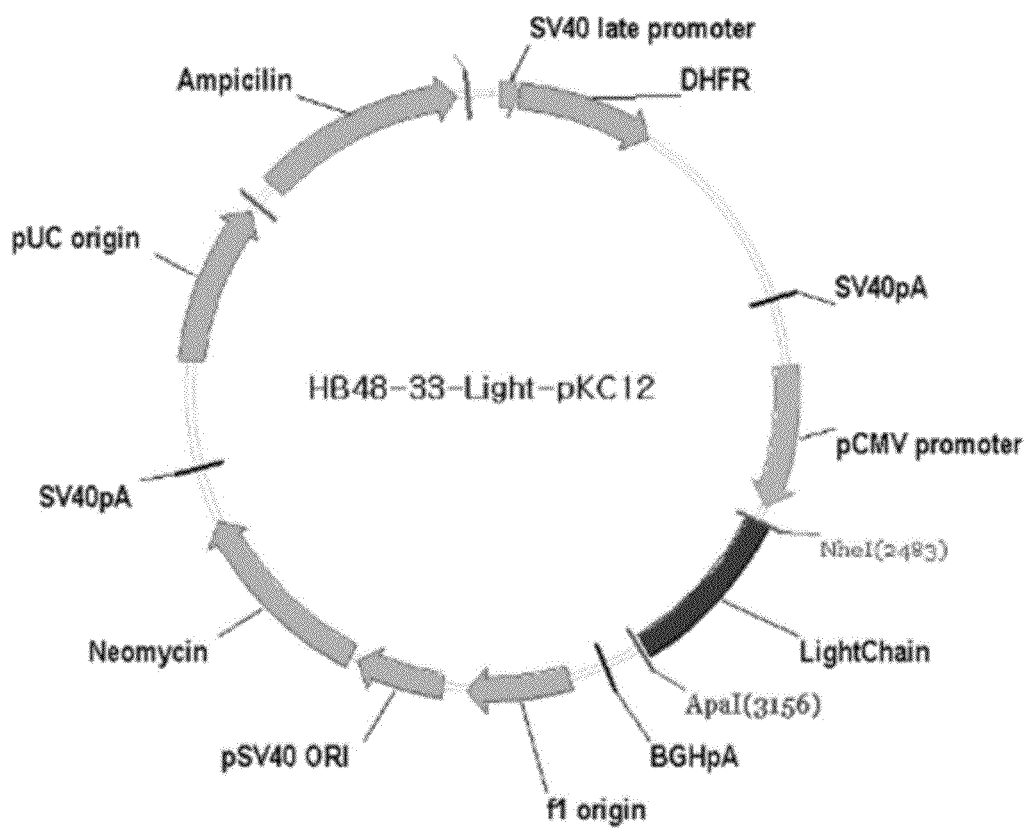
FIGS. 6, 7, and 8: maps of expression vectors for expressing the light chains of the human antibodies of the present invention, HB48-33-Light-pKC12, HB48-35-Light-pKC12, and HB48-59-Light-pKC12, respectively.
Figure 7:
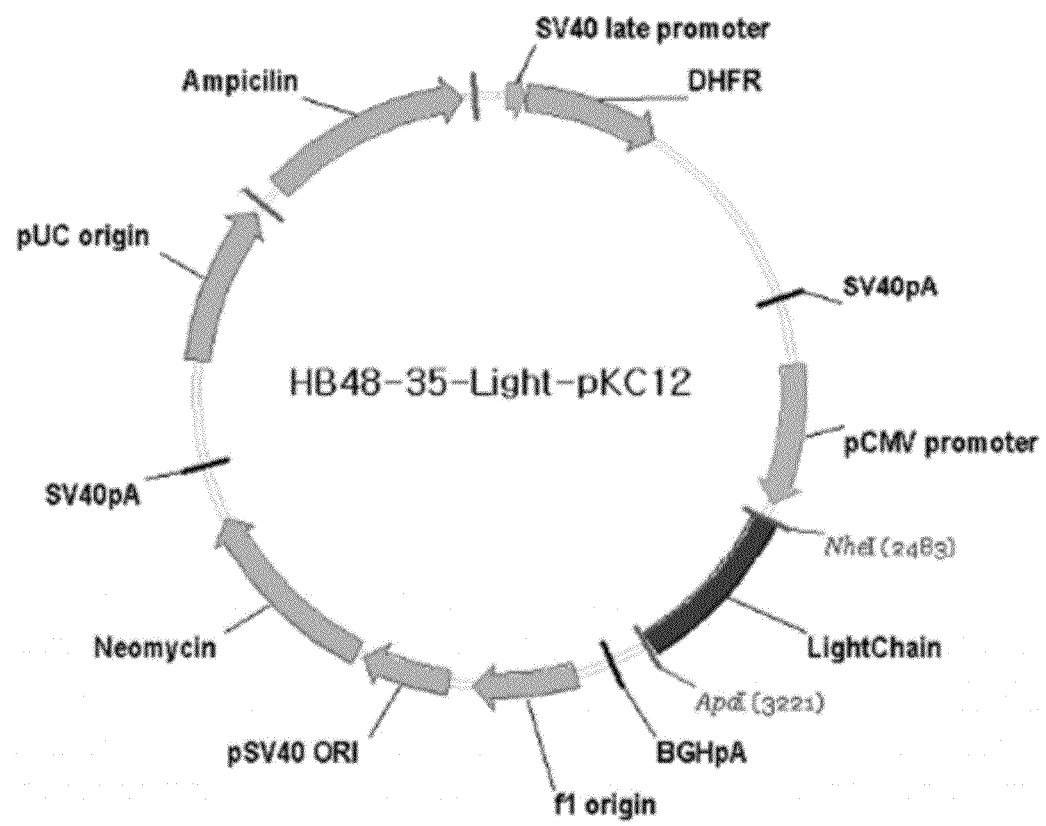
Figure 8:
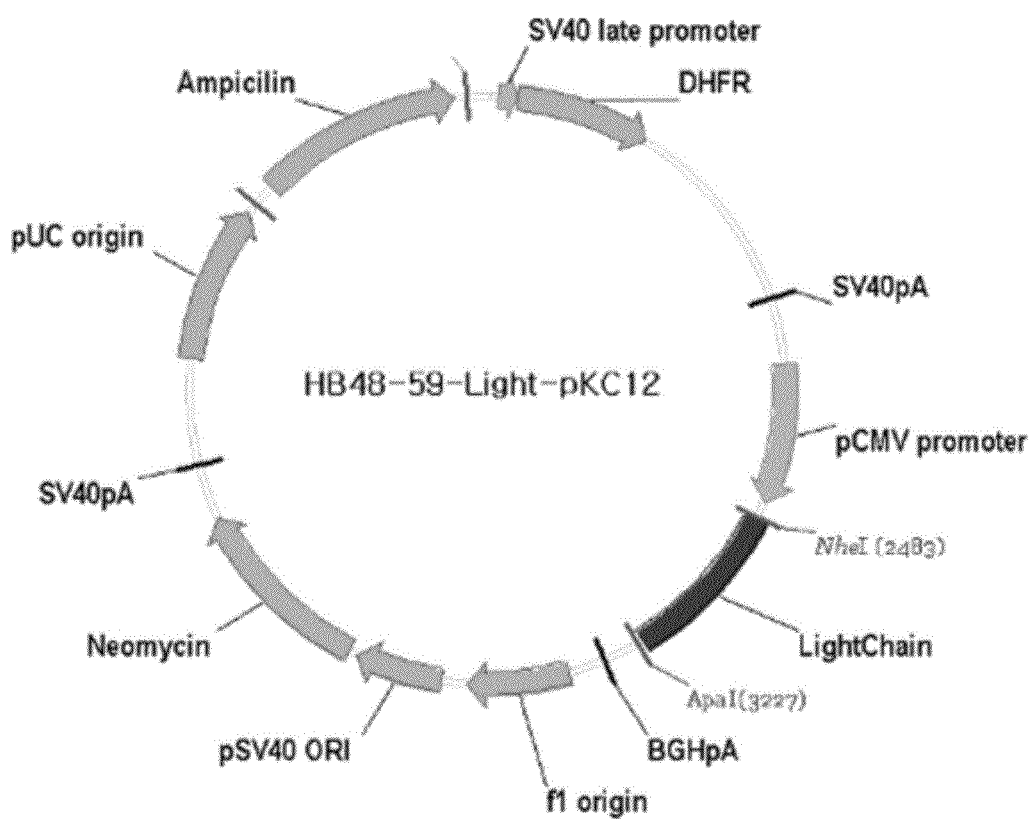

The present invention provides an expression vector for expressing the light chain variable region of the antibody specifically binding to the HBV surface antigen, comprising the DNA encoding the light chain variable region of the antibody. Preferably, the expression vector may be "HB48-33-Light-pKC13" whose map is depicted in FIG. 6, "HB48-35-Light-pKC13" whose map is depicted in FIG. 7, or "HB48-59-Light-pKC13" whose map is depicted in FIG. 8.

Specifically, the vectors may be prepared by inserting each VL fragment (HB48-33VL, HB48-35VL, or HB48-59VL) of the antibodies selected by panning processes into a suitable vector, e.g., pKC12 vector (deposit No. KCLRF-BP-00054; Korean Patent No. 523732).

The present invention provides an animal cell line transformed with the expression vectors for expressing the variable regions of heavy chain and light chains of the inventive antibody. The animal cell line may be CHO (Chinese hamster ovary), HEK 293, or NSO cell line, preferably, CHO (Chinese hamster ovary) cell line.

The antibodies according to the present invention may be prepared by which the variable regions of heavy and light chains are linked to each other.

Figure 12:
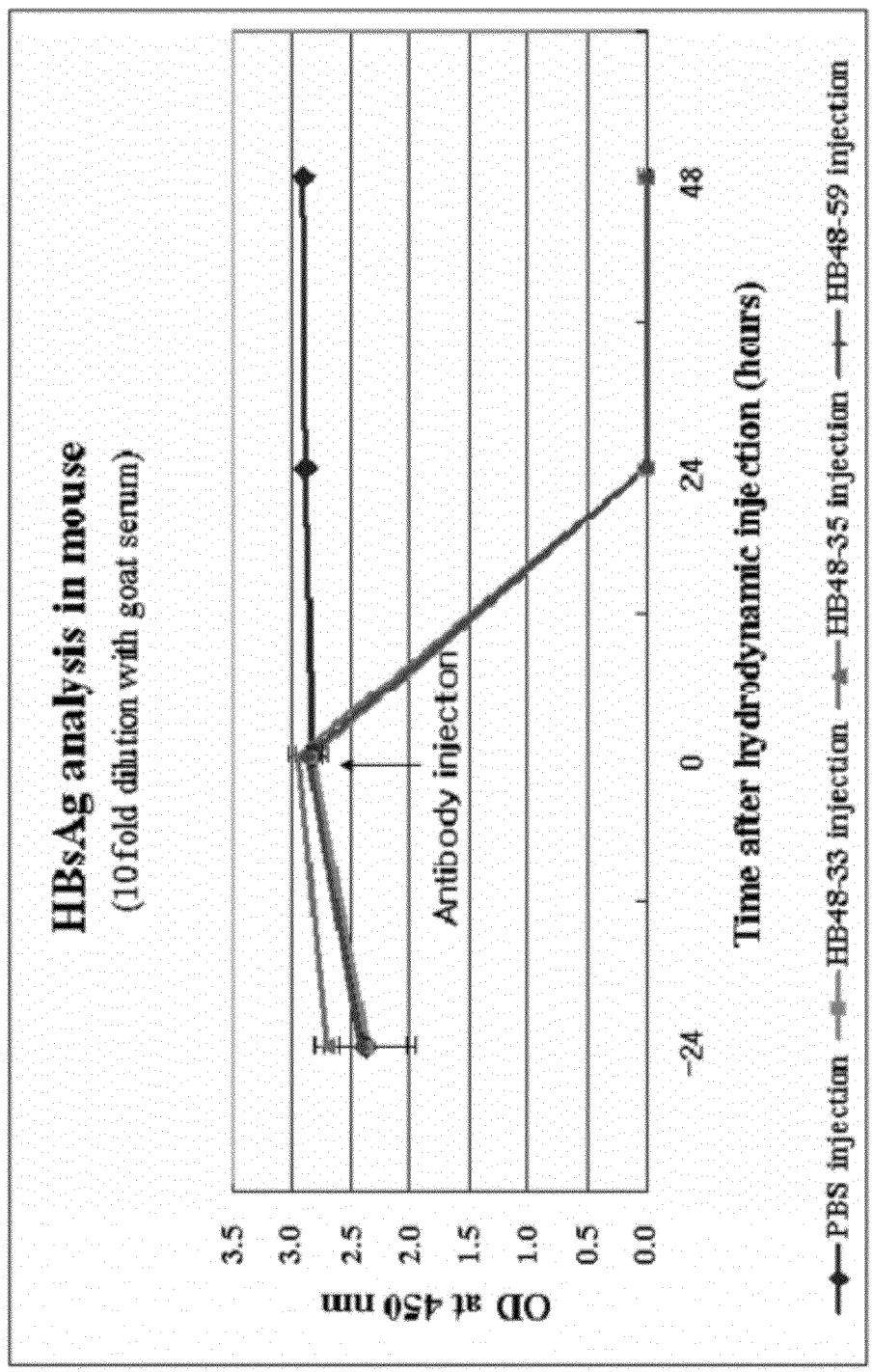
FIG. 12: a graph showing the neutralizing powers of the inventive human antibodies, HB48-33, HB48-35, and HB48-59, which are selected by in vivo efficacy test using a mouse model of acute hepatitis B. It was confirmed that the HBV surface antigen (HBsAg) was expressed 24 hours after injecting the plasmid of FIG. 11, and that the surface antigen was reduced by administration of the inventive antibodies. The surface antigen was measured by Genedia HBsAg ELISA 3.0 (Green Cross MS, Korea).

The affinity of the inventive antibodies to the antigen may be measured, e.g., by the competitive ELISA (Kim et al., Hybridoma, 20, 265-272, 2001). As shown in FIG. 10, the affinity of HB48-35 was highest among the human antibodies of the present invention, whereas those of HB48-59 and HB48-33 were approximately 1.3 and 4.0 fold lower than HB48-35, respectively. Further, in an HBV mouse model, which is prepared by hydrodynamic injection of HBV DNA into C57BL6 mouse to induce hepatitis B-like symptoms (Hydrodynamic injection; Liu et al., Gene Therapy, 6, 1258-1266, 1999), HB48-33, HB48-35, and HB48-59 antibodies showed the neutralizing ability of HBV in which surface antigen of HBV was reduced to a ground level by the antibody in a mouse blood (FIG. 12). Therefore, the antibodies of the present invention may be used for preventing or treating hepatitis B by binding to HBV surface antigen to inactivate HBV.

In view of the result, the present invention provides a pharmaceutical composition for preventing or treating hepatitis B, comprising the antibody. The composition of the present invention may be prepared into a pharmaceutical formulation in accordance with conventional methods. In preparation of the formulation, the antibody is preferably mixed with a carrier or diluted with a carrier, or incorporated within a carrier which may be in the form of a container. When the carrier serves as a diluent, it may be a solid, semisolid, or liquid which acts as a vesicle, excipient, or medium for the antibody. Thus, the formulation may be in the form of tablets, pills, powders, sachets, cachets, elixirs, suspensions, emulsions, solutions, syrups, aerosols, soft and hard gelatin capsules, sterile injectable solutions, sterile powers, and the like. Examples of a suitable carrier, excipient, or diluents include lactose, dextrose, sucrose, sorbitol, mannitol, calcium silicate, cellulose, methyl cellulose, microcrystalline cellulose, polyvinylpyrrolidone, water, methylhydroxybenzoate, propylhydroxybenzoate, talc, magnesium stearate, and mineral oil. The formulations can additionally include filling agents, anticoagulants, lubricating agents, wetting agents, flavoring agents, emulsifying agents, preserving agents, and the like. The antibody composition of the present invention can further comprise interferons, anti-HBV monoclonal antibodies, anti-HBV polyclonal antibodies, nucleoside analogues, DNA polymerase inhibitors, siRNA agents, or vaccines for treatment, as an anti-viral agent, in conjunction with the antibody.

The HBV infection and HBV-associated diseases can be prevented or treated by administering the inventive composition to a mammal including a human. The dosage of the antibody within the composition will depend on the subject, the severity of the disease condition, administration rate, and physician's determination. The antibody as an effective ingredient can be administered to a mammal via a parenteral route in an effective amount ranging from about 0.001 to 10 mg/kg body weight, preferably 0.005 to 1 mg/kg body weight per day, in a single dose or in divided doses. In some cases, a small or large quantity of dose may be suitable, relative to the aforementioned dose, and the large quantity of dose can be administered in divided small doses per day.

The following Examples are given for the purpose of illustration only, and are not intended to limit the scope of the invention.

EXAMPLE 1

Isolation of RNA

In order to select antibodies specifically binding to the HBV surface antigen, a human antibody library was constructed. A mixture of RNAs from human bone marrow, human thymus, human spleen and human B cell was used. All RNAs except for human B cell RNA were purchased from Clontech (U.S.) and human B cell RNA was isolated as follows:

50 mL of blood taken from a healthy adult was diluted by mixing with 50 mL of PBS. 3 mL of Ficoll-Paque PLUS (GE Healthcare, U.S.) was put in a 15 mL tube and 4 mL of the diluted blood was added thereto. The mixture was centrifuged at 3,000 rpm to isolate a white blood cell. 2 mL of the isolated white blood cell was mixed with 6 mL of PBS and centrifuged at 100×g for 10 min. 100 µL of the white blood cell was mixed with 1 mL of Trizole (Life Technology, U.S.) to isolate RNA.

Meanwhile, the isolated RNA was diluted with distilled water, and the absorbance at 260 nm was measured to calculate its amount (1.8 µg/µL; Ultraspec 2000 UV-VIS spectrophotometer, GE, U.S.). Detailed procedure is as follows:

1 mL of trizole was added to 100 µL of white blood cell, shook well, and left at room temperature (15° C. to 30° C.) for 5 min. Then, 200 µL of chloroform was added, shook vigorously for 15 sec, and left at room temperature for 3 min. Subsequently, the mixture was centrifuged under a condition of 2-8° C., 15 min and 15,000 rpm, and the supernatant was transferred into a new tube. 500 µL of isopropyl alcohol was added and mixed well, and left at room temperature for 10 min. Then, the mixture was centrifuged at 2~8° C. and 15,000 rpm for 5 min to remove the supernatant. 1 mL of 75% ethanol was added thereto and the mixture was centrifuged under a condition of 2~8° C., 5 min and 15,000 rpm to remove ethanol, and the RNA pellet was dried at room temperature for 5 min. 150 µL of distilled water was added thereto to suspend the RNA pellet, and the absorbance of the suspension was measured at 260 nm. The remnant was stored at −20° C.

EXAMPLE 2

Amplification of Antibody Genes

1 µg of RNA isolated in Example 1 and 1 µL of pd(T)$_{12-18}$ (0.5 µg/µL) were mixed with distilled water to make final volume into 12.5 µL. The mixture was subjected to a reaction at 70° C. for 2 min and cooled in ice. Then, 5× reaction buffer, 10 mM dNTP mix, recombinant RNase inhibitor and MMLV reverse transcriptase (Clontech, U.S.) were added thereto to make final volume into 20 µL, followed by the reaction at 42° C. for 1 hr and at 95° C. for 5 min to synthesize cDNA. PCR reaction was carried out using LiquiMix QM Premix, Magenta (Neurotics Inc, Korea), 4 µL of cDNA as a template, 19 µL of distilled water, and 1 µL (25 µmol/µL) of primers designed for scFv region, heavy chain variable region and light chain variable region (kappa and lambda), respectively [ScFv: SEQ ID NOs: 9 (Forward), 10 (Reverse-κ), and 11 (Reverse-λ); heavy chain variable region: SEQ ID NOs: 12 (Forward-VH1), 13 (Forward-VH2), 14 (Forward-VH3), 15 (Forward-VH4), 16 (Forward-VH5), 17 (Forward-VH6), 18 (Forward-VH7), 19 (Reverse); light chain variable region κ chain: SEQ ID NOs: 20 (Forward-VK1/3A), 21 (Forward-VK1/3B), 22 (Forward-VK2), 23 (Forward-VK4), 24 (Forward-VK5), 25 (Forward-VK6), 26 (Reverse-JK-A), 27 (Reverse-JK-B), and 28 (Reverse-JK-C); light chain variable region λ chain: SEQ ID NOs: 29 (Forward-VL1~3-A), 30 (Forward-VL1~3-B), 31 (Forward-VL4), 32 (Forward-VL5), 33 (Forward-VL6), 34 (Forward-VL7), 35 (Forward-VL8), 36 (Forward-VL9), 37 (Forward-VL10), 38 (Reverse-JL-A), and 39 (Reverse-JL-B).

PCR reaction was carried out at 95° C. for 5 min, 95° C. for 1 min, 55° C. for 2 min, 72° C. for 2 min with 30 cycles, finally 72° C. for 15 min.

Figure 1:
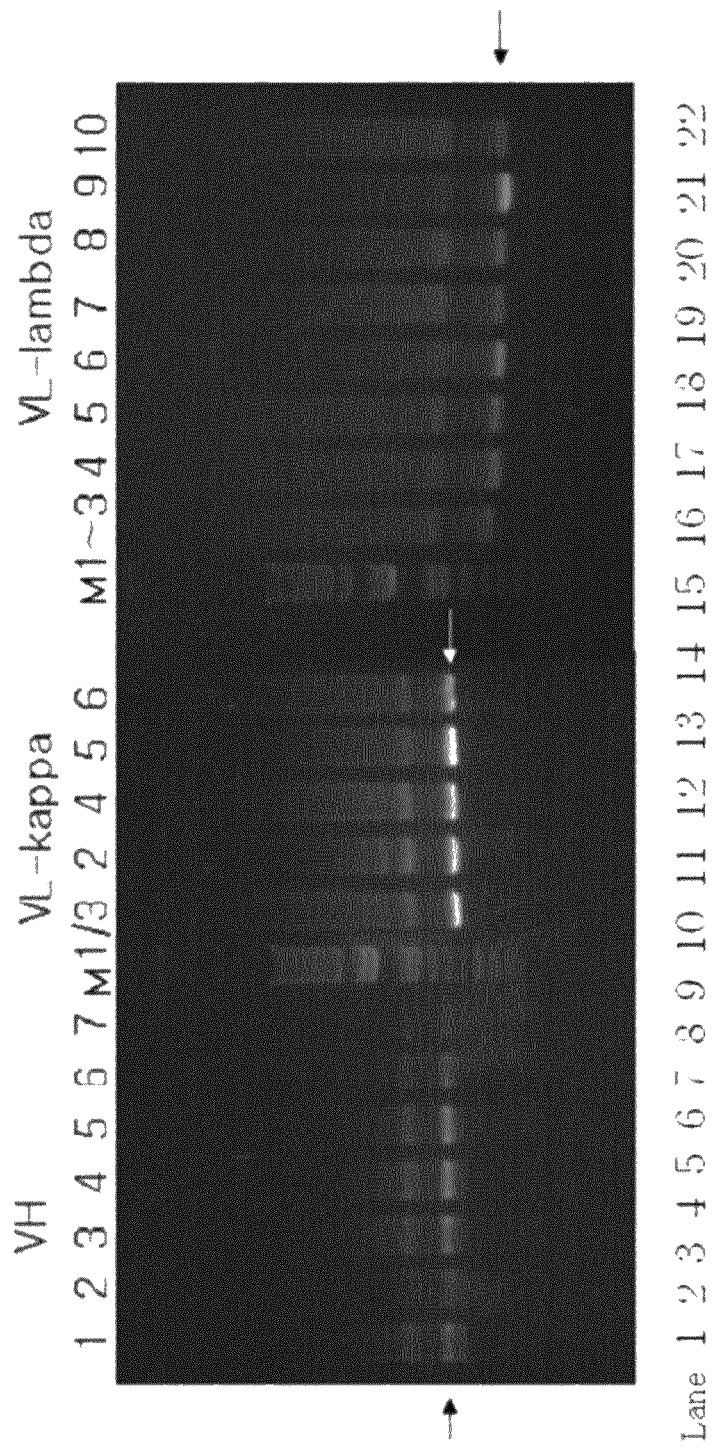
FIG. 1: a photographic result of electrophoresis (1% agarose gel) analysis exhibiting DNAs which respectively encode the inventive heavy chain variable (VH) and the light chain variable regions (VL) synthesized by PCR.

The amplified antibody DNAs were identified by electrophoresis in 1.2% agarose gel (FIG. 1), and purified using Qiagen kit (Qiagen, Germany). As shown in FIG. 1, 350 bp of DNA bands corresponding to variable regions of the heavy and light chains (kappa and lambda) were obtained. In FIG. 1, M refers to a size marker, VH: heavy chain variable region (lane 1: heavy chain variable region type I; lane 2: heavy chain variable region type II; lane 3: heavy chain variable region type III; lane 4: heavy chain variable region type VI; lane 5: heavy chain variable region type V; lane 6: heavy chain variable region type VI; and lane 7: heavy chain variable region type VII), and VL to light chain variable region (lane 9: light chain variable region 1/3κ; lane 10: light chain variable region 2κ; lane 11: light chain variable region 4κ; lane 12: light chain variable region 5κ; lane 13: light chain variable region 6κ; lane 15: light chain variable region 1~3λ; lane 16: light chain variable region 4λ; lane 17: light chain variable region 5λ; lane 18: light chain variable region 6λ; lane 19: light chain variable region 7λ; lane 20: light chain variable region 8λ; lane 21: light chain variable region 9λ; and lane 22: light chain variable region 10λ).

EXAMPLE 3

Restriction Enzyme Digestion of Antibody DNAs

VH and VL (kappa and lambda) prepared in Example 2 were digested with restriction enzymes SfiI/BspEI and BspEI/NotI, respectively, and the digested fragments were isolated from 1.2% agarose gel electrophoresis and purified using Qiagen kit.

EXAMPLE 4

Ligation of the Antibody DNAs and Preparation of Libraries

Phage-display vector pKS4H (Green cross Corp., Korea, see Korean Patent No. 0635370) were digested using a restriction enzyme, SfiI/BspEI, and was separated using 1.2% agarose gel electrophoresis, followed by purification using Qiagen kit. 40 μg of the pKS4H was mixed with 10 μg of VH prepared in Example 3, and T4 DNA ligase (New England BioLabs, U.S.) was added thereto, followed by the reaction overnight at 25° C. The ligation mixture was purified using Qiagen kit, and was transformed into E. coli XL1-blue (Stratagene, U.S.) by electroporation. The transformant was cultured in 100 mL of medium overnight, and the plasmid was isolated. The plasmid was designated as "pKS4H-VH-ΔVL".

Figure 2:
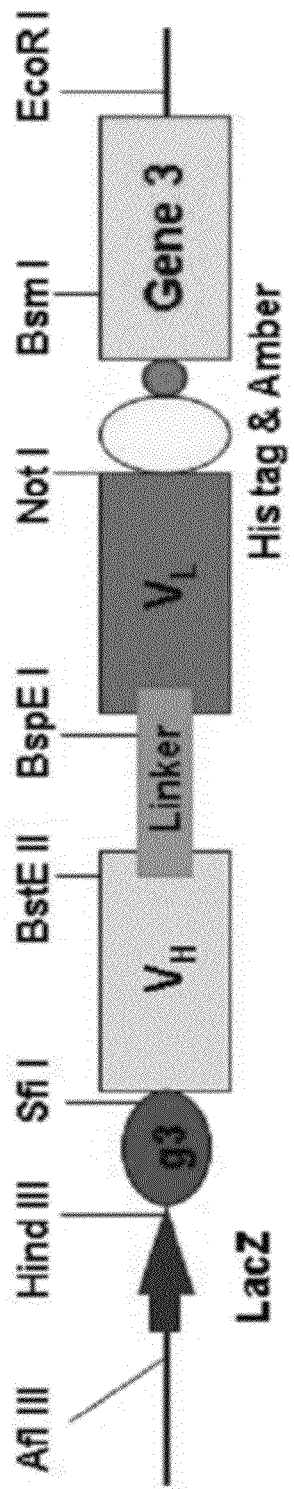
FIG. 2: a map of the phage-display vector pKS4H, comprising the heavy chain variable region and the light chain variable region of the inventive antibody.

The plasmid, pKS4H-VH-ΔVL, was digested with a restriction enzyme, BspEI/NotI, and purified as described above. Then, 40 μg of pKS4H-VH-ΔVL plasmid was mixed with 10 μg of VL PCR DNA prepared in Example 3 and T4 DNA ligase (New England BioLabs, U.S.), and was subjected to a reaction overnight at 25° C. The ligation mixture was purified using Qiagen kit, and was transformed into E. coli XL1-blue by electroporation. The transformant was cultured in 100 mL of medium containing carbenicillin and tetracyclin at 37° C. for 2 hours. Then, M13 helper phage (Stratagene, U.S.) was inoculated to the medium and cultured for 16 hr to prepare a phage library as reported in Engberg et al (*Mol. Biotechnol.*, 6, 287-310, 1995). Meanwhile, a plasmid was isolated from the E. coli, and designated as "pKS4H-VH-VL". The map of the plasmid is depicted in FIG. 2.

EXAMPLE 5

Selection of Antibodies Binding to the HBV Surface Antigen

Figure 3:
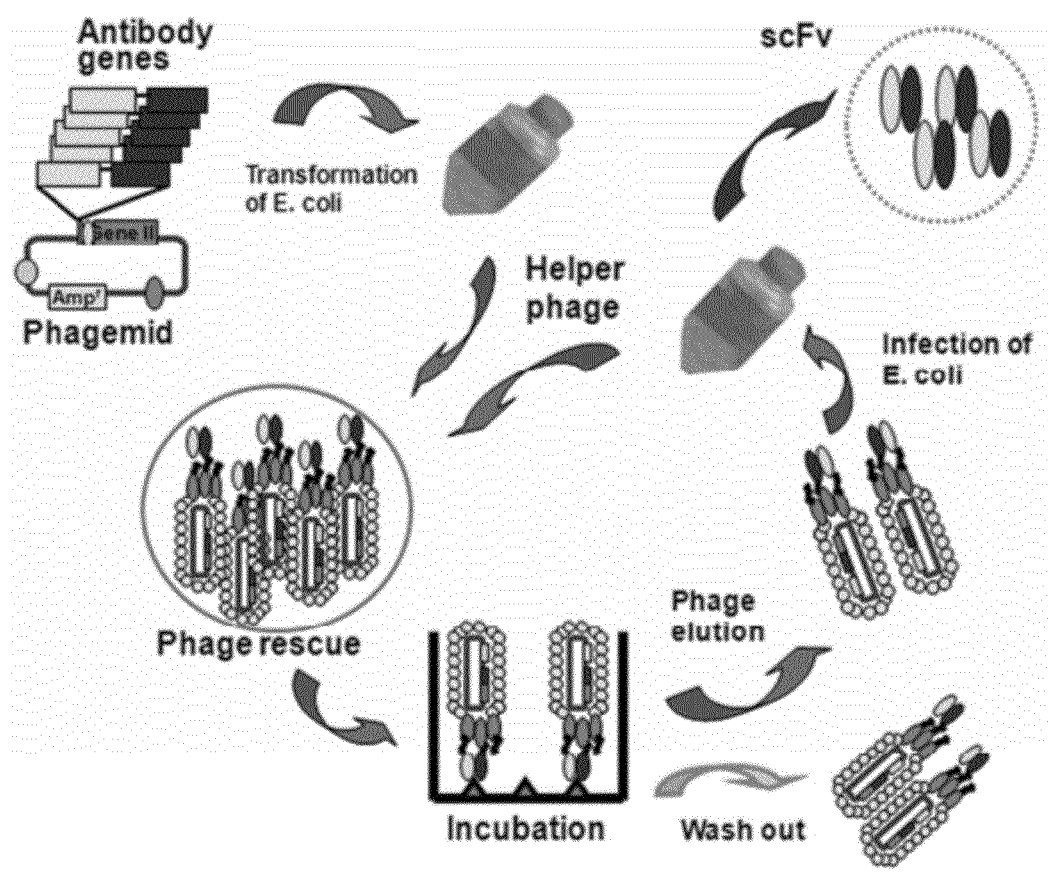
FIG. 3: a diagram showing the process of selecting an antibody from an antibody library using the panning technique.

Antibodies binding to the HBV surface antigen were selected by a modification of panning technique (Engberg et al., *Mol. Biotechnol.*, 6, 287-310, 1996; and Kim et al., *Gene*, 241, 19-25, 2000). Specifically, HBV surface antigen (Green cross Corp., Korea) was diluted with PBS and each immunotube (NUNC, Denmark) was coated with the diluted antigen. Then, the phage library prepared in Example 4 was added to the coated immunotube and incubated for 2 hr at 37° C. Phages binding to HBV were eluted using 0.1M of glycine buffer (pH 2.0). Subsequently, E. coli XL1-blue was infected with the phages and a helper phage was added. The E. coli was incubated overnight and a PEG solution (20% PEG 8,000 and 15% NaCl) was added thereto. Then, precipitated phages were collected (phage rescue) and the phages were again subjected to a reaction with the immunotube coated with the HBV surface antigen, and the above procedure was repeated 4 times. Three human antibodies binding to HBV surface antigen were selected from the procedure, and designated as HB48-33, HB48-35, and HB48-59. The process of selecting human antibodies using phage-display libraries was illustrated in FIG. 3.

Each colony from $4^{th}$ panning was grown in 2 mL of medium, in accordance with a known method (Kim et al., *Gene*, 241, 19-25, 2000), and the expression of antibody was induced by treatment of IPTG (isopropyl β-D-1-thiogalactopyranoside). The expression of antibody was measured by ELISA (Enzyme-Linked ImmunoSorbent Assay), using a 96-well plate coated with HBV surface antigen.

EXAMPLE 6

Sequence Analysis of Selected Antibodies

Colonies which secrete human antibodies HB48-33, HB48-35, and HB48-59 selected in Example 5 were grown overnight in 10 mL of LB medium containing 50 μg/mL of carbenicillin and plasmids were isolated using Qiagen plasmid mini kit (Qiagen, Valencia, Calif., U.S.) therefrom. The plasmids were digested with SfiI/NotI, and electrophoresed in agarose gel so as to identify the insertion of fragments of antibodies. The DNA sequence of scFv inserted into the plasmid was analyzed. The nucleotide sequences of scFv were analyzed with a sequencing primer, p033 of SEQ ID NO: 40 in Genotech (Daejeon, Korea).

The DNA sequences of scFv of human antibodies HB48-33, HB48-35, and HB48-59 were translated into amino acids using a web-based program (www.expasy.org: DNA to Protein translate tool), and the translated amino acid sequences were shown in FIG. 4. As shown in FIG. 4, human antibodies HB48-33, HB48-35, and HB48-59 had heavy chain variable regions represented by same amino acid sequences, and light chain variable regions represented by different amino acid sequences.

EXAMPLE 7

Construction of Expression Vectors

In order to convert the antibody fragments into intact immunoglobulins, antibody expression vectors, pRC13 and pKC12 were used (see Korean Patent No. 523732; Deposit No. KCLRF-BP-00054).

The heavy chain expression vector pRC13 is a vector in which a VH fragment of an antibody can be easily inserted into HindIII and ApaI sites. As exemplified in FIG. 5, the DNAs encoding the heavy chain variable regions of the human antibodies HB48-33, HB48-35, and HB48-59 were amplified by PCR using primers of SEQ ID NOs: 41 (Forward) and 42 (Reverse) under a condition of 95° C. for 1 min, 55° C. for 2 min, 72° C. for 2 min, digested with HindIII/ApaI, and inserted into pRC13 which was digested with same restriction enzymes. The recombinant vector was designated "HB48-33-Heavy-pRC13", "HB48-35-Heavy-pRC13", or "HB48-59-Heavy-pRC13" (see FIG. 5).

Meanwhile, the light chain expression vector pKC12 is a vector in which a VL fragment of an antibody can be easily inserted into NheI and ApaI sites. As exemplified in FIGS. 6, 7, and 8, DNAs encoding the κ light chain variable region of the human antibodies HB48-35 and HB48-59 were amplified by PCR using primers of SEQ ID NOs: 43 (Forward) and 44 (Reverse) under a condition of 95° C. for 1 min, 55° C. for 2 min, 72° C. for 2 min, and DNA encoding the λ light chain variable region of the human antibody HB48-33 was amplified by PCR using primers of SEQ ID NOs: 43 (Forward) and 45 (Reverse) under a condition of 95° C. for 1 min, 55° C. for 2 min, 72° C. for 2 min. The amplified DNAs were digested with NheI/ApaI, and inserted into pKC12 which was digested with same restriction enzymes. The recombinant vectors were designated "HB48-33-Light-pKC12", "HB48-35-Light-pKC12", and "HB48-33-Light-pKC12", respectively (see FIGS. 6, 7, and 8).

EXAMPLE 8

Construction of Animal Cell Lines Secreting Antibodies $2 \times 10^5$ CHO (Chinese hamster ovary) cells were grown in T-25 flask (NUNC, Denmark) filled with α-MEM medium (Life Technologies, U.S.) containing 10% FBS (Life Technologies, U.S.), in 37° C. incubator in the presence of 5% $CO_2$, 24 hours prior to transfection, until confluency reaches 50%. Then, 30 µg of lipofectin (Life Technologies, U.S.) was added to 1.5 mL of opti-MEM (Life Technologies, U.S.) and left undisturbed for 90 min at room temperature. At the same time, 8 µg of HB48-33-Heavy-pRC13 & 7 µg of HB48-33-Light-pKC12, 8 µg of HB48-35-Heavy-pRC13 & 7 µg of HB48-35-Light-pKC12, and 8 µg of HB48-59-Heavy-pRC13 & 7 µg of HB48-59-Light-pKC12 were mixed respectively and added to 15 mL of opti-MEM, then left undisturbed for 90 min at room temperature. After 90 min, the medium containing lipofectin was mixed with the medium containing HB48-33-Heavy-pRC13 & HB48-33-Light-pKC12, HB48-35-Heavy-pRC13 & HB48-35-Light-pKC12, and HB48-59-Heavy-pRC13 & HB48-59-Light-pKC12, respectively, and incubated for 15 min at room temperature. During the reaction, the medium was removed from the cells, and the cells were washed three times with PBS for transfection. The reaction mixture was added to the washed cells and incubated for 6 hours. After 6 hours, the reaction mixture was removed, and α-MEM medium was added and incubated for 48 hours. Then the cells were treated with trypsin (Life Technologies, U.S.) to detach from the flask, diluted with α-MEM medium, and subcultured at 96-well plate (NUNC, Denmark). At the time, the α-MEM medium contains no ribonucleoside and deoxyribonucleoside, whereas contains 10% of dialyzed FBS (Life Technologies, U.S.) and 550 µg/mL of G418 (Sigma, U.S.). The medium was replaced with a fresh medium every two days. The culture supernatant forming colonies was collected for ELISA analysis, and selected cells were transferred into 12-well plate. When the cells grew well in 12-well plate, the cells were transferred into 6-well plate, and when the cells also grew well in E-well plate, methotrexate (MTX, Choong-wae Pharma Corporation, Korea) was treated thereto. The initial concentration of MTX was 20 nM, and increased to 80 nM, 320 nM and 1 µM according to the adaptability of cells. Cell lines which survived at a concentration of 1 µM and had a high amount of antibody secretion were selected. The selected cell lines were mass-cultured in an incubator with 65 rpm, 5% $CO_2$ and 37° C., using spinner flask and serum-free medium. $10^8$ cells were cultured in 250 mL flask filled with 100 mL of serum-free medium. When the number of the cells became 2 times of the initial inoculation, cells were collected by centrifugation at 1,000 rpm for 5 min. The collected cells were cultured again in 500 mL flask filled with 200 mL of medium. When the number of the cells became 2 times the initial inoculation, cells were collected by centrifugation at 1,000 rpm for 5 min, and transferred into 3 L spinner flask filled with 1 L of medium. Sodium butyrate (Aldrich, U.S.) was added thereto to a final concentration of 2 mM, the cells were cultured for 5 days, and the supernatant was collected from the medium. From supernatant collected from spinner flasks, antibodies were purified using a protein A-agarose column (Amersham Pharmacia Biotech, U.S.) and were analyzed by SDS-PAGE.

Figure 9:
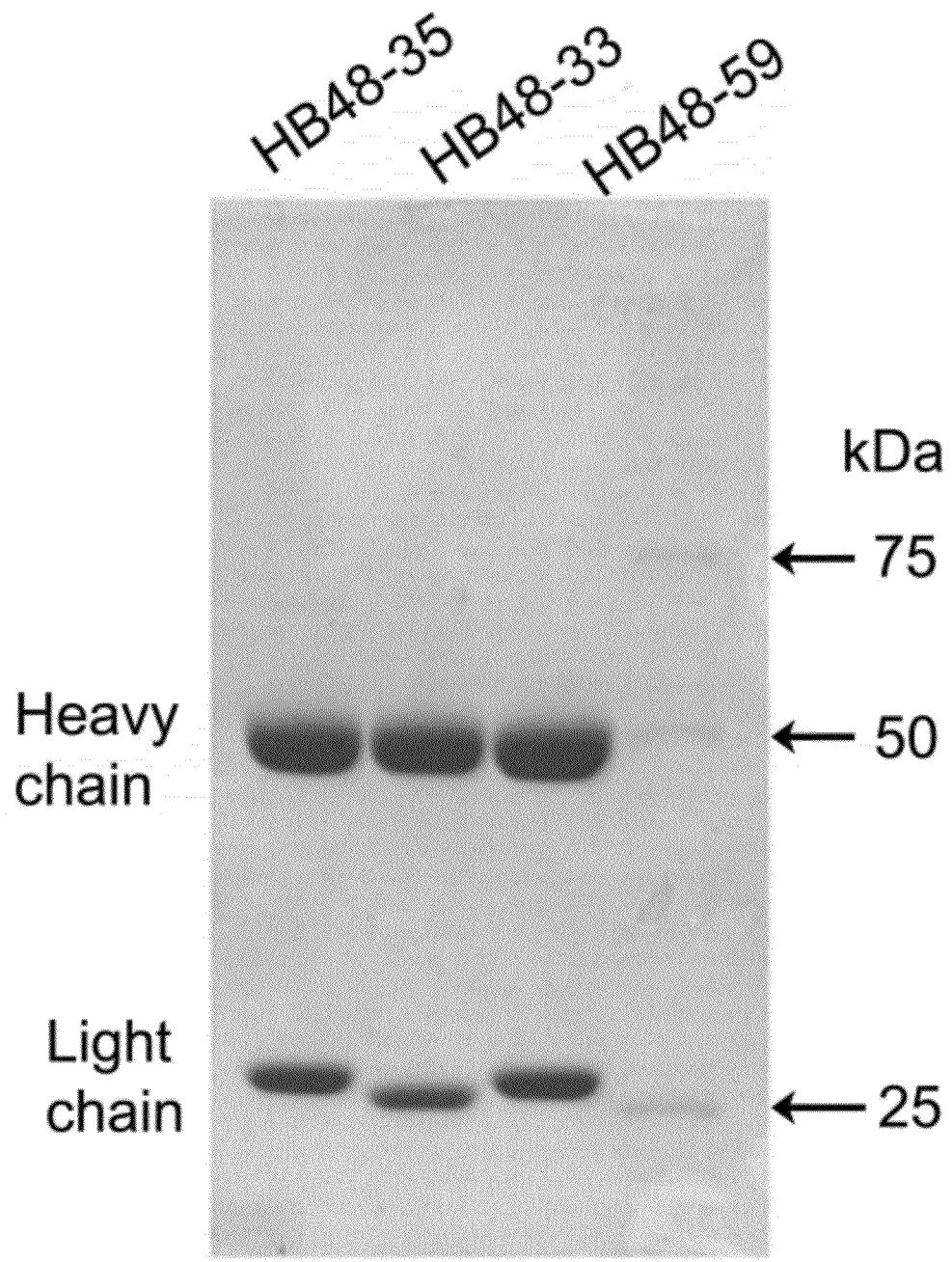
FIG. 9: SDS-PAGE analysis of the heavy chain and light chain expressed from the transformant.

As shown in FIG. 9, about 50 kDa of heavy chain bands and 25 kDa of light chain bands were observed, indicating that antibodies were synthesized correctly.

EXAMPLE 9

Measurement of Antibody Affinity

The affinities of the antibodies obtained in Example 8 to the HBV surface antigen were determined by a competitive ELISA method (Kim et al., *Hybridoma*, 20, 265-272, 2001), and the results were shown in FIG. 10. Brief procedure is as follows:
(1) Determination of Optimum Concentration of Antibodies
  A. Preparation of a Plate
  100 µL of HBV surface antigen (Green cross Corp., Korea) at a 2 µg/mL dilution in PBS was added to each well of an ELISA plate and incubated overnight at 4° C. Each well of the plate was washed once with PBST, 300 µL of 1% BSA-PBS solution was added to each well, and incubated for 1 hour at room temperature.
  B. $1^{st}$ Reaction
  100 µL of each purified antibody (0.5 µg/mL) was added to each well of plate, and incubated for 2 hours at room temperature, and washed four times with PBST.
  C. $2^{nd}$ Reaction
  100 µL of goat anti-human IgG (Fab specific)-perxoidase conjugate (Sigma) at a 1:5000 dilution in 1% BSA-PBS was added to each well, incubated for 1 hour at room temperature, and washed four times with PBST.
  D. Substrate Reaction
  100 µL of TMB (3,3',5,5'-tetramethylbenzidine, Microwell peroxidase substrate system (KPL, MD, U.S.) was added to each well and O.D value was measured at 405 nm. Optimum concentration of antibody was determined as the antibody concentration that gives half-maximum binding.
(2) Competitive ELISA
  A. Preparation of a Plate
  100 µL of HBV surface antigen (Green cross Corp., Korea) at a 2 µg/mL dilution in PBS was added to each well of an ELISA plate and incubated overnight at 4° C. Each well was washed once with PBST, 300 µL of 1% BSA-PBS solution was added to each well, and incubated for 1 hour at room temperature.
  B. $1^{st}$ Reaction
  2 µg of HBV surface antigen was diluted by a two-fold serially and 10 µL of the diluted HBsAg was added to each well of the plate. Then, 90 µL of the antibody diluted to the optimum concentration determined in (1) was added to each well, incubated for 2 hours at room temperature, and washed 4 times with PBST.
  C. $2^{nd}$ Reaction
  100 µL of goat anti-human IgG (Fab specific)-perxoidase conjugate (Sigma) at a 1:5,000 dilution in 1% BSA-PBS was added to each well, incubated for 1 hour at room temperature, and washed four times with PBST.
  D. Substrate Reaction
  100 µL of TMB (3,3',5,5'-tetramethylbenzidine, Microwell peroxidase substrate system (KPL, MD, U.S.) was added to each well and O.D value was measured at 405 nm. The concentration of HBsAg which inhibits 50% of maximum binding (O.D value in which no competing EGFR exists) was determined as Kd.

As shown in FIG. 10, the affinity of HB48-35 was highest among the human antibodies of the present invention, and in contrast those of HB48-59 and HB48-33 were approximately 1.3 and 4.0 fold lower than HB48-35, respectively.

EXAMPLE 10

In Vivo Efficacy Test Using a Mouse Model of Acute Hepatitis B

The neutralizing abilities against HBsAg of HB48-33, HB48-35, and HB48-59 were compared, in a C57BL6 mouse model which is prepared by hydrodynamic injection of HBV DNA to manifest hepatitis B-like symptoms.

Twenty female C57BL6 mice of 4 weeks old and weighing about 20 g, were purchased from Charles Liver Laboratory (MA, U.S.), and were divided into 4 groups of 5 mice as shown in Table 1.

TABLE 1

| Group | Number of mice | Test material and route | Dosage |
| --- | --- | --- | --- |
| Control group | 5 | PBS, intravenous injection | 0.2 mL |
| Exp. group I | 5 | HB48-33 0.1 mg, intravenous injection | 0.2 mL |
| Exp. group II | 5 | HB48-35 0.1 mg, intravenous injection | 0.2 mL |
| Exp. group III | 5 | HB48-59 0.1 mg, intravenous injection | 0.2 mL |

20 μg of vector pHBV-MBRI constructed by inserting HBV DNA into pcDNA3.1 (Invitrogen, U.S.) (Shin et al., *Virus Research* 119, 146-153, 2006; See FIG. 11) were injected into all mice via mouse tail veins in 9.5% of weight by a volume in a speed of 0.3 mL/min to induce an acute hepatitis B. After 24 hours, 0.2 mL of test materials listed in Table 1 were injected via mice tail veins. Serums were isolated at pre-injection (0 hr), 24 hour post-injection, and 48 hour post-injection. The isolated serums were diluted by 10 fold with goat serum, and then the blood concentrations of HBsAg were measured using Genedia HBsAg ELISA 3.0 (Green Cross MS, Korea) and the results are shown in FIG. 12. As shown in FIG. 12, the blood concentration of HBsAg was maintained at maximum point for 48 hours, in the control group intravenously injected with PBS. In contrast, the blood concentration of HBsAg was not detected for 24 to 48 hours, in groups treated with 0.1 mg HB48-33 (experimental group I), 0.1 mg HB48-35 (experimental group II), and 0.1 mg HB48-59 (experimental group III). Accordingly, it was confirmed that the antibodies of the present invention are very effective in neutralizing the HBV surface antigen.

While the invention has been described with respect to the above specific embodiments, it should be recognized that various modifications and changes may be made to the invention by those skilled in the art which also fall within the scope of the invention as defined by the appended claims.

What is claimed is:

1. A human antibody specifically binding to hepatitis B virus surface antigen, comprising:
   a) a heavy chain variable region having the amino acid sequence of SEQ ID NO: 1;
   b) a light chain variable region having any of the amino acid sequences of SEQ ID NOs: 2, 3, and 4;
   c) a heavy chain constant region; and
   d) a light chain constant region.

2. A pharmaceutical composition comprising the antibody of claim 1 and a pharmaceutically acceptable carrier.

* * * * *

SEQUENCE LISTING

```
<160> NUMBER OF SEQ ID NOS: 45

<210> SEQ ID NO 1
<211> LENGTH: 117
<212> TYPE: PRT
<213> ORGANISM: Artificial Sequence
<220> FEATURE:
<223> OTHER INFORMATION: Synthesized heavy chain variable region of
      HB48-33, HB48-35 or HB48-59 antibody

<400> SEQUENCE: 1

Gln Val Gln Leu Val Gln Ser Gly Gly Glu Val Lys Lys Pro Gly Ala
  1               5                  10                  15

Leu Met Lys Val Ser Cys Lys Ala Ser Gly Tyr Ile Phe Thr Ser Tyr
                 20                  25                  30

Gly Ile Ser Trp Val Arg Gln Ala Pro Gly Gln Gly Leu Glu Trp Ile
             35                  40                  45

Gly Trp Ile Asn Thr Tyr Ser Gly His Thr Asn Tyr Ala Arg Lys Phe
         50                  55                  60

Arg Gly Arg Val Thr Met Thr Trp Asp Thr Ser Thr Ser Thr Ala Tyr
     65                  70                  75                  80

Met Glu Leu Ser Ser Leu Arg Ser Asp Asp Thr Ala Val Tyr Tyr Cys
                 85                  90                  95

Ala Arg Val Pro Thr Trp Gly Ile Asp Tyr Trp Gly Gln Gly Thr Leu
                100                 105                 110

Val Thr Val Ser Ser
            115

<210> SEQ ID NO 2
<211> LENGTH: 107
<212> TYPE: PRT
```

```
<213> ORGANISM: Artificial Sequence
<220> FEATURE:
<223> OTHER INFORMATION: Synthesized light chain variable region of
      HB48-33 antibody

<400> SEQUENCE: 2

Gln Ala Gly Leu Thr Gln Pro Pro Ser Val Ser Val Ala Pro Gly Lys
 1               5                  10                  15

Thr Ala Arg Ile Thr Cys Gly Gly Asp Asn Ile Gly Arg Lys Ser Val
            20                  25                  30

His Trp Tyr Gln Gln Lys Thr Gly Gln Ala Pro Val Leu Val Val Tyr
        35                  40                  45

Glu Asp Asn Lys Arg Pro Ser Gly Ile Pro Glu Arg Phe Ser Gly Ser
50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Val Val
                85                  90                  95

Phe Gly Gly Gly Thr Lys Leu Thr Val Leu Gly
            100                 105

<210> SEQ ID NO 3
<211> LENGTH: 108
<212> TYPE: PRT
<213> ORGANISM: Artificial Sequence
<220> FEATURE:
<223> OTHER INFORMATION: Synthesized light chain variable region of
      HB48-35 antibody

<400> SEQUENCE: 3

Glu Ile Val Leu Thr Gln Ser Pro Pro Ser Leu Ser Ala Ser Val Gly
 1               5                  10                  15

Asp Arg Val Thr Ile Thr Cys Gln Ala Ser Gln Asp Ile Asn Asn Asn
            20                  25                  30

Val Asn Trp Phe Gln Gln Glu Pro Gly Lys Ala Pro Arg Leu Leu Ile
        35                  40                  45

Tyr Asp Ala Ser Asn Leu Gln Thr Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Thr Ser Val Tyr Pro Leu
                85                  90                  95

Thr Phe Gly Gly Gly Thr Lys Val Asp Ile Lys Arg
            100                 105

<210> SEQ ID NO 4
<211> LENGTH: 114
<212> TYPE: PRT
<213> ORGANISM: Artificial Sequence
<220> FEATURE:
<223> OTHER INFORMATION: Synthesized light chain variable region of
      HB48-59 antibody

<400> SEQUENCE: 4

Asp Ile Val Met Thr Gln Thr Pro Leu Ser Leu Pro Val Thr Pro Gly
 1               5                  10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45
```

```
Pro Gln Leu Leu Ile Tyr Leu Gly Ser Lys Arg Ala Ser Gly Val Pro
        50                  55                  60

Asp Arg Phe Ser Gly Ser Gly Ser Gly Thr Asp Phe Thr Leu Gln Ile
 65                  70                  75                  80

Ser Arg Val Glu Ala Glu Asp Val Gly Val Tyr Tyr Cys Met Gln Ser
                85                  90                  95

Thr Gln Phe Pro Pro Tyr Thr Phe Gly Gln Gly Thr Lys Leu Glu Ile
            100                 105                 110

Lys Arg

<210> SEQ ID NO 5
<211> LENGTH: 351
<212> TYPE: DNA
<213> ORGANISM: Artificial Sequence
<220> FEATURE:
<223> OTHER INFORMATION: Synthetic construct encoding heavy chain
      variable region of HB48-33, HB48-35 or HB48-59 antibody

<400> SEQUENCE: 5
caggtgcagc tggtgcagtc tgggggtgag gtgaagaagc ctggggcctt aatgaaggtc      60
tcctgcaagg cttctggtta catctttacc agttatggta tcagctgggt gcgacaggcc     120
cctggacaag gcttgagtg gataggatgg atcaacactt acagtggtca cacaaactat     180
gcacggaagt tccggggag agtcaccatg acctgggaca cgtccaccag cacagcctac     240
atggagctga gcagcctgag atctgacgac acggccgtct attactgtgc gagagtccca     300
acgtggggta ttgactactg gggccaggga accctggtca ccgtctcctc a              351

<210> SEQ ID NO 6
<211> LENGTH: 321
<212> TYPE: DNA
<213> ORGANISM: Artificial Sequence
<220> FEATURE:
<223> OTHER INFORMATION: Synthetic construct encoding light chain
      variable region of HB48-33 antibody

<400> SEQUENCE: 6
caggcagggc tgactcagcc accctcagtg tcagtggccc caggaaagac ggcccggatt      60
acctgtgggg gagacaacat tggaagaaaa agtgtgcact ggtaccagca gaagacaggc     120
caggcccctg tgctggtcgt ctatgaagat aacaagcggc cctcagggat acctgagcga     180
ttctctggct ccaactctgg gaacacagcc actctgacca tcagcgggac ccaggctatg     240
gatgaggctg actattactg tcaggcgtgg gacagcagca ctgtggtatt cggcggaggg     300
accaagctga ccgtcctagg t                                                321

<210> SEQ ID NO 7
<211> LENGTH: 324
<212> TYPE: DNA
<213> ORGANISM: Artificial Sequence
<220> FEATURE:
<223> OTHER INFORMATION: Synthetic construct encoding light chain
      variable region of HB48-35 antibody

<400> SEQUENCE: 7
gaaattgtgt tgacgcagtc tccaccctcc ctgtctgcat ctgtaggaga cagagtcacc      60
atcacttgcc aggcgagtca ggacattaat aacaatgtaa attggtttca gcaggaacca     120
gggaaagccc ctaggctcct gatctacgat gcatccaatt tgcaaacagg ggtcccatca     180
aggttcagtg gaagtggatc tgggacagaa ttcactctca ccatcagcag tctgcaacct     240
```
gaagattttg caacttatta ctgtcaacag actagtgttt accctctcac tttcggcgga      300
gggaccaagg tggatatcaa acgt                                             324

<210> SEQ ID NO 8
<211> LENGTH: 342
<212> TYPE: DNA
<213> ORGANISM: Artificial Sequence
<220> FEATURE:
<223> OTHER INFORMATION: Synthetic construct encoding light chain
      variable region of HB48-59 antibody

<400> SEQUENCE: 8
gatattgtga tgacccagac tccactctcc ctgcccgtca cccctggaga gccggcctcc       60
atctcctgca ggtctagtca gagcctcctg catagtaatg gatacaacta tttggattgg      120
tacctgcaga agccagggca gtctccacag ctcctgatct atttgggttc taagcgggcc      180
tccggggtcc ctgacaggtt cagtggcagt ggatcaggca cagatttcac actgcaaatt      240
agtagagtgg aggctgagga tgttggggtt tattactgca tgcaatctac acaatttcca      300
ccgtacactt ttggccaggg gaccaagctg gagatcaaac gt                         342

<210> SEQ ID NO 9
<211> LENGTH: 36
<212> TYPE: DNA
<213> ORGANISM: Artificial Sequence
<220> FEATURE:
<223> OTHER INFORMATION: scFv-forward primer

<400> SEQUENCE: 9
gttgttcctt tctatgcggc ccagccggcc atggcc                                 36

<210> SEQ ID NO 10
<211> LENGTH: 30
<212> TYPE: DNA
<213> ORGANISM: Artificial Sequence
<220> FEATURE:
<223> OTHER INFORMATION: scFv-reverse primer for light chain variable
      kappa

<400> SEQUENCE: 10
gagtcattct cgacttgcgg ccgcacgttt                                        30

<210> SEQ ID NO 11
<211> LENGTH: 27
<212> TYPE: DNA
<213> ORGANISM: Artificial Sequence
<220> FEATURE:
<223> OTHER INFORMATION: scFv-reverse primer for light chain variable
      lambda

<400> SEQUENCE: 11
gagtcattct cgacttgcgg ccgcacc                                           27

<210> SEQ ID NO 12
<211> LENGTH: 39
<212> TYPE: DNA
<213> ORGANISM: Artificial Sequence
<220> FEATURE:
<223> OTHER INFORMATION: VH1-forward primer

<400> SEQUENCE: 12
cagccggcca tggcccaggt gcagctggtg cagtctggg                              39

<210> SEQ ID NO 13
<211> LENGTH: 39
<212> TYPE: DNA
<213> ORGANISM: Artificial Sequence
<220> FEATURE:
<223> OTHER INFORMATION: VH2-forward primer

<400> SEQUENCE: 13
cagccggcca tggcccagrt caccttgaag gagtctggt                    39

<210> SEQ ID NO 14
<211> LENGTH: 39
<212> TYPE: DNA
<213> ORGANISM: Artificial Sequence
<220> FEATURE:
<223> OTHER INFORMATION: VH3-forward primer

<400> SEQUENCE: 14
cagccggcca tggccsaggt gcagctggtg gagtctggg                    39

<210> SEQ ID NO 15
<211> LENGTH: 39
<212> TYPE: DNA
<213> ORGANISM: Artificial Sequence
<220> FEATURE:
<223> OTHER INFORMATION: VH4-forward primer

<400> SEQUENCE: 15
cagccggcca tggcccaggt gcagctgcag gagtcgggc                    39

<210> SEQ ID NO 16
<211> LENGTH: 39
<212> TYPE: DNA
<213> ORGANISM: Artificial Sequence
<220> FEATURE:
<223> OTHER INFORMATION: VH5-forward primer

<400> SEQUENCE: 16
cagccggcca tggccgaggt gcagctggtg cagtctgga                    39

<210> SEQ ID NO 17
<211> LENGTH: 39
<212> TYPE: DNA
<213> ORGANISM: Artificial Sequence
<220> FEATURE:
<223> OTHER INFORMATION: VH6-forward primer

<400> SEQUENCE: 17
cagccggcca tggcccaggt acagctgcag cagtcaggt                    39

<210> SEQ ID NO 18
<211> LENGTH: 39
<212> TYPE: DNA
<213> ORGANISM: Artificial Sequence
<220> FEATURE:
<223> OTHER INFORMATION: VH7-forward primer

<400> SEQUENCE: 18
cagccggcca tggcccaggt gcagctggtg caatctgag                    39

<210> SEQ ID NO 19
<211> LENGTH: 45
<212> TYPE: DNA
<213> ORGANISM: Artificial Sequence
<220> FEATURE:
<223> OTHER INFORMATION: VH-reverse primer

<400> SEQUENCE: 19
cgatccgcca cctccggagc cacctccgcc tgaaccgcct ccacc                45

<210> SEQ ID NO 20
<211> LENGTH: 48
<212> TYPE: DNA
<213> ORGANISM: Artificial Sequence
<220> FEATURE:
<223> OTHER INFORMATION: VK1/3A-forward primer

<400> SEQUENCE: 20
ggtggctccg gaggtggcgg atcggacatc cagatgaccc agtctcca             48

<210> SEQ ID NO 21
<211> LENGTH: 48
<212> TYPE: DNA
<213> ORGANISM: Artificial Sequence
<220> FEATURE:
<223> OTHER INFORMATION: VK1/3B-forward primer

<400> SEQUENCE: 21
ggtggctccg gaggtggcgg atcggaaatt gtgttgacgc agtctcca             48

<210> SEQ ID NO 22
<211> LENGTH: 51
<212> TYPE: DNA
<213> ORGANISM: Artificial Sequence
<220> FEATURE:
<223> OTHER INFORMATION: VK2-forward primer

<400> SEQUENCE: 22
ggtggctccg gaggtggcgg atcggatatt gtgatgaccc agactccact c         51

<210> SEQ ID NO 23
<211> LENGTH: 48
<212> TYPE: DNA
<213> ORGANISM: Artificial Sequence
<220> FEATURE:
<223> OTHER INFORMATION: VK4-forward primer

<400> SEQUENCE: 23
ggtggctccg gaggtggcgg atcggacatc gtgatgaccc agtctcca             48

<210> SEQ ID NO 24
<211> LENGTH: 48
<212> TYPE: DNA
<213> ORGANISM: Artificial Sequence
<220> FEATURE:
<223> OTHER INFORMATION: VK5-forward primer

<400> SEQUENCE: 24
ggtggctccg gaggtggcgg atcggaaacg acactcacgc agtctcca             48

<210> SEQ ID NO 25
<211> LENGTH: 48
<212> TYPE: DNA
<213> ORGANISM: Artificial Sequence
<220> FEATURE:
<223> OTHER INFORMATION: VK6-forward primer

<400> SEQUENCE: 25
ggtggctccg gaggtggcgg atcggawrtt gtgmtgactc agtctcca             48

<210> SEQ ID NO 26
<211> LENGTH: 39

<212> TYPE: DNA
<213> ORGANISM: Artificial Sequence
<220> FEATURE:
<223> OTHER INFORMATION: Jk-A-reverse primer

<400> SEQUENCE: 26
tcgacttgcg gccgcacgtt tgatwtccac yttggtccc                    39

<210> SEQ ID NO 27
<211> LENGTH: 39
<212> TYPE: DNA
<213> ORGANISM: Artificial Sequence
<220> FEATURE:
<223> OTHER INFORMATION: JK-B-reverse primer

<400> SEQUENCE: 27
tcgacttgcg gccgcacgtt tgatctccas cttggtccc                    39

<210> SEQ ID NO 28
<211> LENGTH: 39
<212> TYPE: DNA
<213> ORGANISM: Artificial Sequence
<220> FEATURE:
<223> OTHER INFORMATION: JK-C-reverse primer

<400> SEQUENCE: 28
tcgacttgcg gccgcacgtt taatctccag tcgtgtccc                    39

<210> SEQ ID NO 29
<211> LENGTH: 48
<212> TYPE: DNA
<213> ORGANISM: Artificial Sequence
<220> FEATURE:
<223> OTHER INFORMATION: VL1~3-A-forward primer

<400> SEQUENCE: 29
ggtggctccg gaggtggcgg atcgcagtct gysctgactc agccaccc          48

<210> SEQ ID NO 30
<211> LENGTH: 48
<212> TYPE: DNA
<213> ORGANISM: Artificial Sequence
<220> FEATURE:
<223> OTHER INFORMATION: VL1~3-B-forward primer

<400> SEQUENCE: 30
ggtggctccg gaggtggcgg atcgtcctat gagctgacwc agccaccc          48

<210> SEQ ID NO 31
<211> LENGTH: 48
<212> TYPE: DNA
<213> ORGANISM: Artificial Sequence
<220> FEATURE:
<223> OTHER INFORMATION: VL4-forward primer

<400> SEQUENCE: 31
ggtggctccg gaggtggcgg atcgcwgcyt gtgctgactc agycvycs          48

<210> SEQ ID NO 32
<211> LENGTH: 48
<212> TYPE: DNA
<213> ORGANISM: Artificial Sequence
<220> FEATURE:
<223> OTHER INFORMATION: VL5-forward primer

<400> SEQUENCE: 32
ggtggctccg gaggtggcgg atcgcagsct gtgctgactc agccabct                48

<210> SEQ ID NO 33
<211> LENGTH: 48
<212> TYPE: DNA
<213> ORGANISM: Artificial Sequence
<220> FEATURE:
<223> OTHER INFORMATION: VL6-forward primer

<400> SEQUENCE: 33
ggtggctccg gaggtggcgg atcgaatttt atgctgactc agccccac                48

<210> SEQ ID NO 34
<211> LENGTH: 48
<212> TYPE: DNA
<213> ORGANISM: Artificial Sequence
<220> FEATURE:
<223> OTHER INFORMATION: VL7-forward primer

<400> SEQUENCE: 34
ggtggctccg gaggtggcgg atcgcagrct gtgactcagg agccctca                48

<210> SEQ ID NO 35
<211> LENGTH: 48
<212> TYPE: DNA
<213> ORGANISM: Artificial Sequence
<220> FEATURE:
<223> OTHER INFORMATION: VL8-forward primer

<400> SEQUENCE: 35
ggtggctccg gaggtggcgg atcgcagact gtggtgaccc aggagcca                48

<210> SEQ ID NO 36
<211> LENGTH: 48
<212> TYPE: DNA
<213> ORGANISM: Artificial Sequence
<220> FEATURE:
<223> OTHER INFORMATION: VL9-forward primer

<400> SEQUENCE: 36
ggtggctccg gaggtggcgg atcgcagcct gtgctgactc agccacct                48

<210> SEQ ID NO 37
<211> LENGTH: 48
<212> TYPE: DNA
<213> ORGANISM: Artificial Sequence
<220> FEATURE:
<223> OTHER INFORMATION: VL10-forward primer

<400> SEQUENCE: 37
ggtggctccg gaggtggcgg atcgcaggca gggctgactc agccaccc                48

<210> SEQ ID NO 38
<211> LENGTH: 42
<212> TYPE: DNA
<213> ORGANISM: Artificial Sequence
<220> FEATURE:
<223> OTHER INFORMATION: JL-A-reverse primer

<400> SEQUENCE: 38
ttctcgactt gcggccgcac ctaggacggt sascttggtc cc                      42

<210> SEQ ID NO 39
<211> LENGTH: 42
<212> TYPE: DNA
<213> ORGANISM: Artificial Sequence

```
<220> FEATURE:
<223> OTHER INFORMATION: JL-B-reverse primer

<400> SEQUENCE: 39
ttctcgactt gcggccgcac cgaggacggt cagctgggtg cc                          42

<210> SEQ ID NO 40
<211> LENGTH: 24
<212> TYPE: DNA
<213> ORGANISM: Artificial Sequence
<220> FEATURE:
<223> OTHER INFORMATION: P033 (scFv sequencing primer)

<400> SEQUENCE: 40
caacgtgaaa aaattattat tcgc                                              24

<210> SEQ ID NO 41
<211> LENGTH: 60
<212> TYPE: DNA
<213> ORGANISM: Artificial Sequence
<220> FEATURE:
<223> OTHER INFORMATION: Forward primer for PCR of heavy chain variable
      region

<400> SEQUENCE: 41
ggagacccaa gcttggtacc gagctcggat ccactagtaa cggccgccag tgtgctggaa       60

<210> SEQ ID NO 42
<211> LENGTH: 42
<212> TYPE: DNA
<213> ORGANISM: Artificial Sequence
<220> FEATURE:
<223> OTHER INFORMATION: Reverse primer for PCR of heavy chain variable
      region

<400> SEQUENCE: 42
gaagaccgat gggcccttgg tggaggctga ggagacggtg ac                          42

<210> SEQ ID NO 43
<211> LENGTH: 45
<212> TYPE: DNA
<213> ORGANISM: Artificial Sequence
<220> FEATURE:
<223> OTHER INFORMATION: Forward primer for PCR of light chain (kappa &
      lambda)

<400> SEQUENCE: 43
tagggagacc cgctagcgga gcaagatgga ttcacaggcc caggt                       45

<210> SEQ ID NO 44
<211> LENGTH: 45
<212> TYPE: DNA
<213> ORGANISM: Artificial Sequence
<220> FEATURE:
<223> OTHER INFORMATION: Reverse primer for PCR of light chain (kappa)

<400> SEQUENCE: 44
tatagaatag ggcccccccct cgaggtcgac ctaacactct cccct                      45

<210> SEQ ID NO 45
<211> LENGTH: 51
<212> TYPE: DNA
<213> ORGANISM: Artificial Sequence
```

```
<220> FEATURE:
<223> OTHER INFORMATION: Reverse primer for PCR of light chain (lambda)

<400> SEQUENCE: 45
atagaatagg gcccccctc gaggtcgaca tgaacattct gtaggggcca c          51
```